(12) United States Patent
Rolff

(10) Patent No.: US 11,754,525 B2
(45) Date of Patent: Sep. 12, 2023

(54) GAS DETECTOR WITH AN IONIZING DEVICE

(71) Applicant: INFICON GmbH, Cologne (DE)

(72) Inventor: Norbert Rolff, Horrem (DE)

(73) Assignee: INFICON GmbH, Cologne (DE)

( * ) Notice: Subject to any disclaimer, the term of this patent is extended or adjusted under 35 U.S.C. 154(b) by 0 days.

(21) Appl. No.: 17/431,996

(22) PCT Filed: Feb. 13, 2020

(86) PCT No.: PCT/EP2020/053756
§ 371 (c)(1),
(2) Date: Aug. 18, 2021

(87) PCT Pub. No.: WO2020/169446
PCT Pub. Date: Aug. 27, 2020

(65) Prior Publication Data
US 2022/0136997 A1 May 5, 2022

(30) Foreign Application Priority Data

Feb. 19, 2019 (DE) .......................... 102019202242.1

(51) Int. Cl.
| | |
|---|---|
| *G01R 31/00* | (2006.01) |
| *G01N 27/62* | (2021.01) |
| *G01N 33/00* | (2006.01) |
| *H03F 3/45* | (2006.01) |

(52) U.S. Cl.
CPC ......... *G01N 27/62* (2013.01); *G01N 33/0027* (2013.01); *H03F 3/45475* (2013.01); *H03F 2203/45528* (2013.01)

(58) Field of Classification Search
USPC ........................... 324/464; 73/24.25, 204.25
See application file for complete search history.

(56) References Cited

U.S. PATENT DOCUMENTS

| 4,806,765 A | 2/1989 | Heinen | |
| 4,996,876 A * | 3/1991 | Krause | ..................... G01P 5/12 |
| | | | 73/204.25 |
| 2006/0244526 A1 | 11/2006 | Mijuskovic | |

(Continued)

FOREIGN PATENT DOCUMENTS

| DE | 19833453 A1 | 10/2000 |
| DE | 19960798 A1 | 7/2001 |

(Continued)

*Primary Examiner* — Vincent Q Nguyen
(74) *Attorney, Agent, or Firm* — The Webb Law Firm

(57) ABSTRACT

The disclosure provides a gas detector with an ionizing device for producing ions depending on a gas to be detected. The gas detector includes a catcher for receiving the electrical current produced by the ions, and a measuring device with an electrical measuring resistor. The electrical measuring resistor produces an electrical measuring potential from the current and is surrounded, at least in part, by an electrical shield resistor, denoted by $R_T$. The same potentials, up to a deviation of at most 25%, are applied in the longitudinal direction of the electrical measuring resistor to mutually opposed regions of the electrical measuring resistor and the electrical shield resistor.

12 Claims, 3 Drawing Sheets

(56) References Cited

U.S. PATENT DOCUMENTS

| | | | |
|---|---|---|---|
| 2006/0251543 A1* | 11/2006 | Koratkar | ............... G01N 30/64 422/98 |
| 2014/0166878 A1 | 6/2014 | Wright et al. | |
| 2015/0357981 A1 | 12/2015 | Lerche | |

FOREIGN PATENT DOCUMENTS

| | | |
|---|---|---|
| DE | 10152606 C1 | 4/2003 |
| EP | 0219557 B1 | 1/1990 |
| GB | 2424330 A | 9/2006 |

\* cited by examiner

GAS DETECTOR WITH AN IONIZING DEVICE

CROSS-REFERENCE TO RELATED APPLICATIONS

This application is the United States national phase of International Application No. PCT/EP2020/053756 filed Feb. 13, 2020, and claims priority to German Patent Application No. 10 2019 202 242.1 filed Feb. 19, 2019, the disclosures of which are hereby incorporated by reference in their entirety.

BACKGROUND

Field of the Invention

The disclosure relates to a gas detector with an ionizing device for producing ions depending on a gas type to be detected and for producing an electrical potential depending on the ions.

Description of Related Art

The ionizing device can be a mass spectrometer, such as a sector field mass spectrometer or a quadrupole mass spectrometer for measuring partial pressure or an ionization vacuum meter for measuring total pressure. Such ionizing devices are designed to produce ions depending on certain gas types. The ion current produced by the ions is received by a catcher.

A measuring device which produces a measurable measuring potential from the ion current is used to measure the produced ion current. For this purpose, the measuring device has a current amplifier, for example, with an operational amplifier, in order to amplify the ion current. A measurable electrical measuring potential is produced from the amplified current by means of an electrical measuring resistor, for example, in the feedback of the operational amplifier.

In fast vacuum applications, the previous current amplifiers in the frequently used lower current range are the slowest link in the signal chain. According to the disclosure, this disadvantage is to be avoided.

Furthermore, applications are known in which the ion current is amplified using an electron multiplier. The response time can thereby be reduced, but with less stability.

Particularly, it is conventionally necessary to use high-ohm resistors with small currents, said resistors having a significant capacitance to the surroundings. If the surroundings of the measuring resistor are connected to ground potential, there will be a superelevation when there is a signal jump. If, on the other hand, part of the surroundings of the measuring resistor lies on the output signal of the current amplifier, the output signal increases slowly.

The measuring resistors conventionally used to measure the current produced from the ions have a high resistance in the range of around 500 gigaohms in order to keep the noise component in the measuring signal low. A high-ohm measuring resistor produces undesirable parasitic stray capacitances.

SUMMARY

The disclosure is based on the object of creating an improved gas detector with an ionizing device.

The gas detector according to the disclosure has an ionizing device of the type described above. According to the disclosure, the measuring resistor is surrounded at least in part by an electrical shield resistor and the same potentials up to a deviation of at most 25% are applied in the longitudinal direction of the measuring resistor to mutually opposed regions of the measuring resistor and the shield resistor. As a result, a comparable or nearly identical voltage drop prevails across the shield resistor as across the measuring resistor. The parasitic stray capacitances are therefore without current.

Both the measuring resistor and the electrical shield resistor have mutually opposed outer ends which each serve to make electrical contact with the resistors. Almost the same potentials should be applied at the two ends of the measuring resistor as at the corresponding ends of the shield resistor. In other words, this means that at the first end of the measuring resistor, approximately, that is, up to a deviation of at most 25%, the same potential is applied as at the first end of the shield resistor. The same potential as at the second end of the shield resistor is applied at the second end of the measuring resistor, up to a deviation of at most 25%. As a result, the same potential should drop across the measuring resistor and across the shield resistor in a spatially distributed manner.

In this case, the one end of the measuring resistor is preferably electrically connected to the one end of the shield resistor, so that the same potential is applied at the two ends. The respective other ends of the measuring resistor and the shield resistor can then be at ground potential up to a deviation of at most 25%. The deviation of at most 25% can result, for example, from the fact that the respective end of the measuring resistor is connected to ground by means of the input side of an operational amplifier, so that the potential difference corresponding to the input voltage of the operational amplifier still falls between the relevant connection of the measuring resistor and the ground potential.

The resistance value of the shield resistor should be lower than the resistance value of the measuring resistor. For example, the resistance value of the shield resistor can be a maximum of 1 megaohm, while the resistance value of the measuring resistor can be above 100 gigaohm. The shield resistor is then designed to be of low resistance and itself causes negligible stray capacitances.

The dimensions of the shield resistor are advantageously similar to those of the measuring resistor in order to bring about the same voltage drop at the shield resistor as at the measuring resistor. The measuring resistor is typically elongated in form with a length that is greater than the width and height thereof. The total length of the shield resistor is preferably greater than the length of the measuring resistor. The sections of the shield resistor protruding beyond the measuring resistor then have the same potential.

The shield resistor can be a cylinder that surrounds the measuring resistor and is pushed over the measuring resistor for this purpose. The cylindrical shield resistor can be a carbon tube, for example, in order to achieve the desired low-ohm resistance value in addition to the desired geometric dimensions.

Alternatively, the shield resistor can be formed as a chain of a plurality of electrical conductors, each of which at least in part surrounds the measuring resistor. Low-ohm individual resistors are arranged between adjacent conductors. A first end of the chain has the same electrical potential as the first end of the measuring resistor. The opposite second end of the chain, on the other hand, has the same potential as the opposite second end of the measuring resistor. The parts of the shield resistor that protrude beyond the measuring resistor have the same potentials as the ends of the measuring resistor. The individual resistors preferably each have a resistance value of at most 100 kilohms.

The electrical conductors advantageously each have a section that is curved or angled around the measuring resistor.

BRIEF DESCRIPTION OF THE DRAWINGS

In the following, embodiments of the disclosure are explained in more detail with reference to the figures. Shown are.

DETAILED DESCRIPTION OF THE INVENTION

Figure 1:
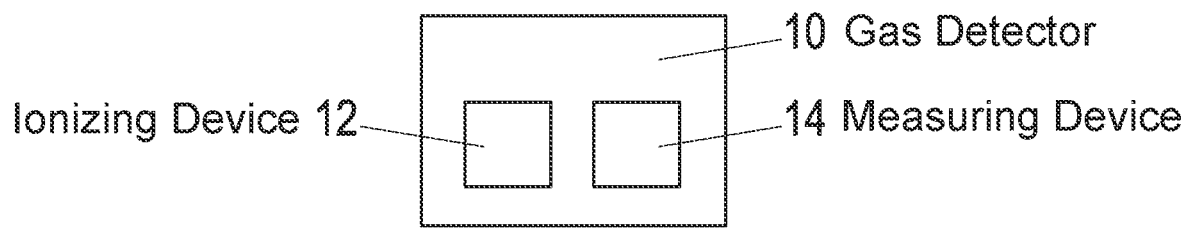
FIG. 1 a schematic block diagram,
FIG. 2 a first embodiment in a perspective view,
FIG. 3 the view according to arrow III in FIG. 2,
FIG. 4 the view according to FIG. 3 of a second embodiment,
FIG. 5 the view according to FIG. 3 of a third embodiment and
FIG. 6 a circuit diagram of the first embodiment.

In FIG. 1, it can be seen that the gas detector 10 has an ionizing device 12 and a measuring device 14. The ionizing device can be a mass spectrometer. A detail of the measuring device is shown in more detail in FIG. 2.

Figure 2:
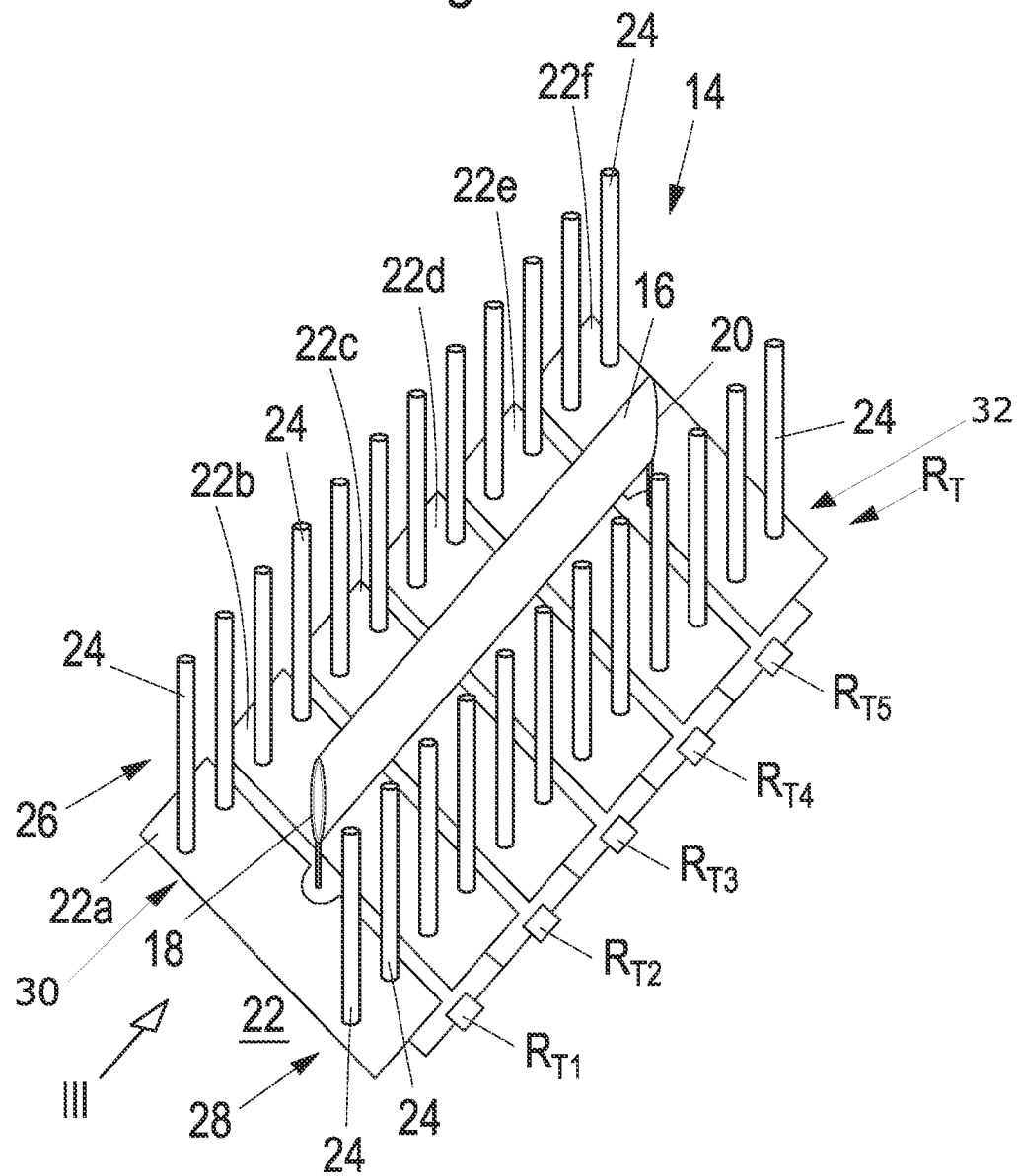

The measuring device 14 has an operational amplifier, not shown in FIG. 2, for amplifying the measuring current, with a measuring resistor 16. The measuring resistor 16 is an elongated component in the present case, cylindrical with an oval cross-section. The length of the measuring resistor is greater than its width and height. A first frontal end 18 and a second frontal end 20 of the measuring resistor opposite the first end 18 are electrically connected to the operational amplifier and supported on a surface 22 with electrical conductors below the measuring resistor 16.

Adjacent to the measuring resistor 16, an electrical shield resistor $R_T$ is formed from a plurality of electrical conductors 22a to 22f and 24, low-ohm individual resistors $R_{T1}$, $R_{T2}$, $R_{T3}$, $R_{T4}$ and $R_{T5}$ being arranged between adjacent conductors 24 and electrically connected to the conductors 24. The electrical conductors 24 are each designed as vertically protruding pin posts and are arranged in two rows 26, 28 on mutually opposed sides of the measuring resistor 16. The two rows 26, 28 are arranged straight, parallel to one another and parallel to the measuring resistor 16 at equal distances from the measuring resistor 16. Opposite conductors 24 are electrically connected to one another and thus form a chain of a plurality of electrical conductor pairs with conductors 24. The one end 30 of the chain has the same electrical potential as the one end 18 of the measuring resistor 16. Since the measuring resistor has to receive the measuring current at the end 18, said measuring resistor is not electrically connected to the partial area 22a. The other, opposite end 32 of the chain has the same potential as the other end 20 of the measuring resistor 16.

The electrical conductor pairs with the conductors 24 are arranged as a double pair, the conductor pairs from the conductors 24 each being connected in the longitudinal direction of the measuring resistor 16 to form a double pair. Adjacent partial areas 22a, 22b, 22c, 22d, 22e and 22f are connected to one another by means of one of the individual resistors $R_{T1}$-$R_{T5}$. Due to the resulting voltage drop across the respective individual resistor, the adjacent partial areas and the associated electrical conductors 24 of adjacent double pairs are at different electrical potentials.

Figure 3:
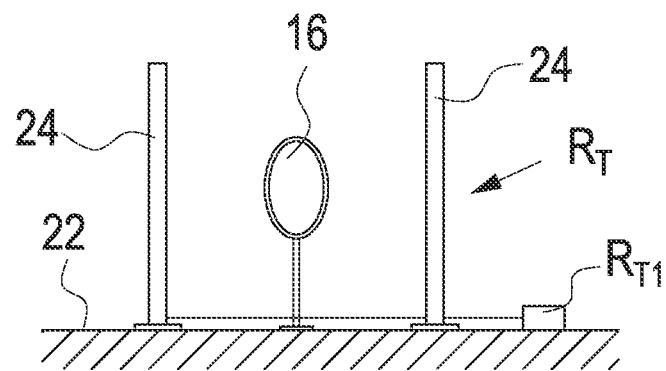

The electrical conductors 24 shield the measuring resistor 16 on laterally opposite sides. The measuring resistor 16 is shielded below by the electrically conductive partial areas 22a-22f. In the first embodiment, the upper side of the measuring resistor 16 opposite the surface 22 is not shielded, as can be seen in FIG. 3.

Figure 4:
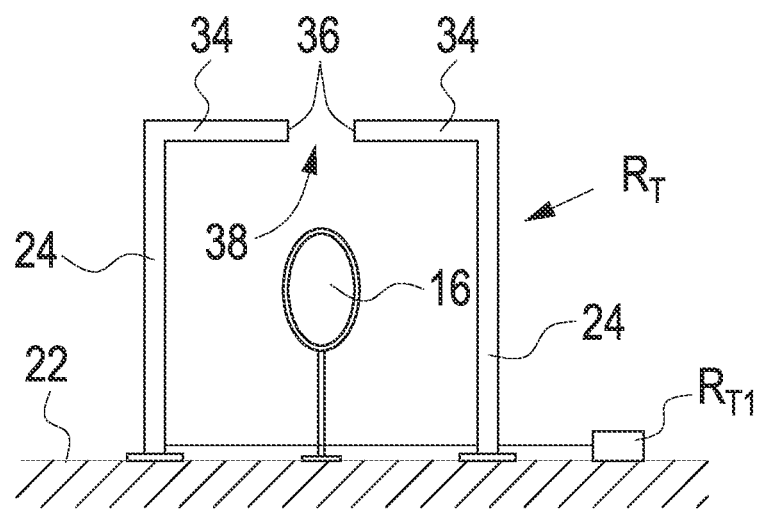

In order to also shield the upper side of the measuring resistor 16, the electrical conductors 24 of the second embodiment shown in FIG. 4 each have an angled section 34. Each electrical conductor is thus L-shaped in form. The angled sections 34 of the same row 26 or 28 are aligned parallel to one another and in the same way. The ends 36 of the electrical conductors 24 of different rows 26, 28 are, as can be seen in FIG. 4, aligned with one another. A small gap 38 remains between the ends 36 of the electrical conductors of different rows 26, 28.

In FIG. 2, the pin posts of the electrical conductors are cylindrical in form. Alternatively, other shapes of the electrical conductors 24 are conceivable, for example, as flat wall piece-like elements, the width of which corresponds, for example, to the width of an electrically conductive partial surface 22a-22f. Preferably, only a small gap for electrical insulation remains in the longitudinal direction between the adjacent partial areas and the adjacent conductors 24 of a row 26, 28, while on the other hand, the flat design of the partial areas and the conductors 24 achieve a large shielding.

The conductors from rows 26 and 28 can thereby each consist of a contiguous curved conductor. Furthermore, from the two rows of pin posts, two pin posts can be respectively connected to one another in the longitudinal direction. Half of the $R_T$ resistors are thereby required.

Figure 5:
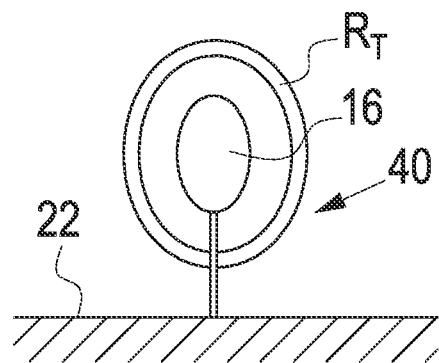

In the embodiment in FIG. 5, instead of the electrical conductors 24, a shield resistor $R_T$ designed as a cylinder 40 is provided, which shield resistor completely surrounds the measuring resistor 16 in the circumferential direction.

Figure 6:
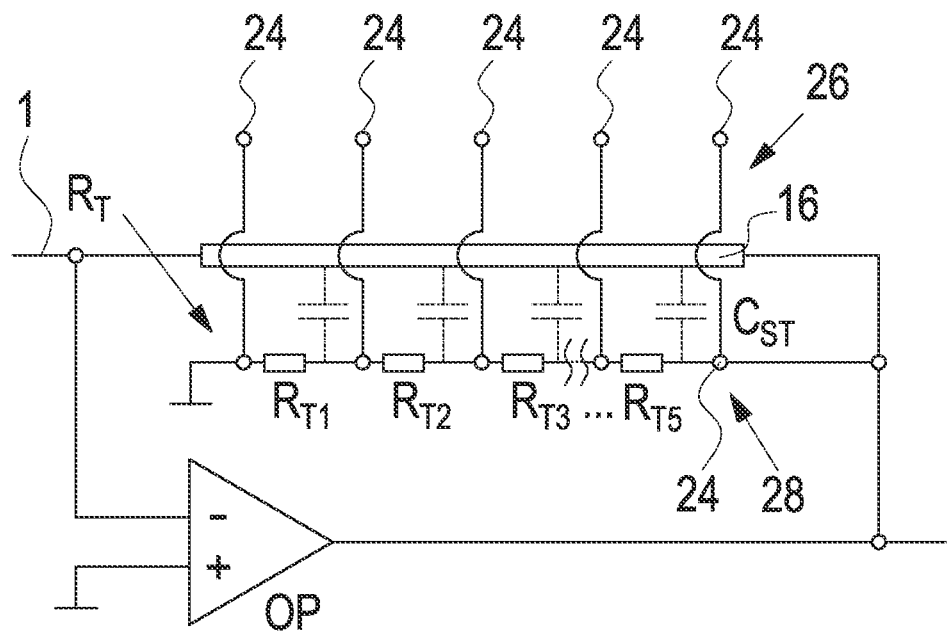

FIG. 6 shows an electrical circuit diagram of the measuring device 14 according to the first embodiment according to FIG. 2. It can be seen that the length of the shield resistor $R_T$ corresponds to or exceeds the total length of the measuring resistor 16. The measuring resistor 16 and the shield resistor $R_T$ are a component of the feedback path of the operational amplifier OP. Each of the individual resistors $R_{T1}$-$R_{T5}$ has a resistance value in the range of a few kiloohms.

A shield resistor $R_T$ formed from five individual resistors is shown in the embodiments. This number of individual resistors is only an example. Individual resistors are preferably arranged between each adjacent electrical partial area. It is conceivable that, as in FIG. 2, only every nth partial area is connected to the respective adjacent partial area by means of an individual resistor, while the remaining adjacent partial areas are connected to one another without a separate resistor.

The embodiment in FIGS. 2 and 6 shows a shield resistor $R_T$, the total length of which is greater than the length of the measuring resistor 16. Alternatively, it is conceivable that the total length of the shield resistor $R_T$ is the same as the length of the measuring resistor 16. For this purpose, further partial areas with associated pairs of further electrical conductors 24 can be arranged in the regions protruding beyond the two frontal ends 18, 20 of the measuring resistor 16. Said additional partial areas should be at the same potential due to an electrically conductive connection.

In addition, electrical shielding (not shown in the figures) of each frontal end 18, 20 of the measuring resistor 16 is conceivable, for example, in the form of an electrically conductive, vertically protruding wall in the region of each frontal end 18, 20. Each of said protruding walls should then be connected to an associated electrical partial area or be at the same potential as said partial area.

The invention claimed is:

1. A gas detector comprising:
   an ionizing device for producing a plurality of ions depending on a detected gas, with a catcher for receiving an electrical current produced by the plurality of ions; and
   a measuring device with an electrical measuring resistor which produces an electrical measuring potential from the electrical current,
   wherein the electrical measuring resistor is surrounded at least in part by an electrical shield resistor, denoted by $R_T$,
   wherein a same potential is applied to mutually opposed regions of the electrical measuring resistor and the electrical shield resistor, denoted by $R_T$, up to a deviation of at most 25%,
   wherein the electrical shield resistor, denoted by $R_T$, is formed as a chain of a plurality of electrical conductors, each of which surround at least in part the electrical measuring resistor,
   wherein a plurality of individual resistors, denoted by $R_{T1} \ldots R_{TN}$, are arranged between a plurality of adjacent electrical conductors,
   wherein one end of the chain has the same potential as the one end of the electrical measuring resistor and another end of the chain has the same potential as the other end of the electrical measuring resistor, and
   wherein, in each case, two of the plurality of electrical conductors are arranged in pairs on mutually opposing sides of the electrical measuring resistor on an electrically conductive partial surface on the surface below the electrical measuring resistor and are electrically connected thereto.

2. The gas detector according to claim 1, wherein one of two ends of the electrical measuring resistor is electrically connected to one of two ends of the electrical shield resistor, denoted by $R_T$, so that said ends have the same potential.

3. The gas detector according to claim 2, wherein the respective other ends of the electrical measuring resistor and the electrical shield resistor, denoted by $R_T$, are at ground potential up to a deviation of at most 25%.

4. The gas detector according to claim 1, wherein the electrical shield resistor, denoted by $R_T$, has a lower resistance value than the electrical measuring resistor.

5. The gas detector according to claim 1, wherein the resistance value of the electrical shield resistor, denoted by $R_T$, is a maximum of one megohm and the resistance value of the electrical measuring resistor is greater than 1 gigaohm.

6. The gas detector, according to claim 1, wherein the electrical measuring resistor is elongated with a length which is greater than a height and a width thereof, wherein the electrical shield resistor, denoted by $R_T$, extends over at least a predominant part of the length of the electrical measuring resistor.

7. The gas detector, according to claim 6, wherein a length of the electrical shield resistor, denoted by $R_T$, is greater than the length of the electrical measuring resistor, wherein a part of the electrical shield resistor having different potentials, denoted by $R_T$, is as long as an active region of the electrical measuring resistor, while sections of the shield resistor protruding beyond the measuring resistor have the same potential.

8. The gas detector according to claim 1, wherein the plurality of electrical conductors are each designed as pin posts.

9. The gas detector according to claim 1, wherein the plurality of electrical conductors protrude on mutually opposed sides of the electrical measuring resistor.

10. The gas detector according to claim 1, wherein each of the plurality of electrical conductors have a section which is curved or angled around the electrical measuring resistor.

11. The gas detector according to claim 1, wherein two adjacent electrical conductors of the plurality of electrical conductors are each electrically connected together to form a double pair.

12. The gas detector according to claim 1, wherein the electrical shield resistor, denoted by $R_T$, is designed as a cylinder surrounding the electrical measuring resistor.

* * * * *